United States Patent [19]

Rosenstein

[11] Patent Number: 5,591,645
[45] Date of Patent: Jan. 7, 1997

[54] SOLID PHASE CHROMATOGRAPHIC IMMUNOASSAY

[75] Inventor: Robert W. Rosenstein, Ellicott City, Md.

[73] Assignee: Becton, Dickinson & Co., Franklin Lakes, N.J.

[21] Appl. No.: 49,247

[22] Filed: Apr. 20, 1993

Related U.S. Application Data

[63] Continuation of Ser. No. 818,000, Dec. 30, 1991, abandoned, which is a continuation of Ser. No. 31,023, Mar. 27, 1987, abandoned.

[51] Int. Cl.$^6$ .................. G01N 33/543; G01N 33/544; G01N 33/538; G01N 33/558
[52] U.S. Cl. .................. 436/514; 436/518; 436/524; 436/528; 436/541; 436/810; 436/829; 435/7.1; 435/810; 435/805; 435/970; 435/287.7; 435/287.8; 435/287.9; 422/56; 422/58; 422/60
[58] Field of Search .................. 435/7.92–7.95, 435/970, 310, 7.1, 805; 436/501, 514, 515, 518, 523, 524, 541, 810, 829, 528; 422/56, 58, 60, 57

[56] References Cited

U.S. PATENT DOCUMENTS

| | | | |
|---|---|---|---|
| 4,094,647 | 6/1978 | Deutsch et al. | 435/4 |
| 4,168,146 | 9/1979 | Grubb et al. | 435/7.92 |
| 4,435,504 | 3/1984 | Zuk et al. | 435/7.91 |
| 4,446,232 | 5/1984 | Liotta | 435/7.93 |
| 4,461,829 | 7/1984 | Greenquist | 435/7.72 |
| 4,552,839 | 11/1985 | Gould et al. | 436/536 |
| 4,668,619 | 5/1987 | Greenquist et al. | 435/7.7 |
| 4,690,907 | 9/1987 | Hibino et al. | 436/514 |
| 4,703,017 | 10/1987 | Campbell et al. | 436/501 |
| 4,708,933 | 11/1987 | Huang et al. | 436/531 |
| 4,717,676 | 1/1988 | Wagner et al. | 436/518 X |
| 4,743,560 | 5/1988 | Campbell et al. | 436/501 |
| 4,770,853 | 9/1988 | Berstein | 422/58 |
| 4,806,312 | 2/1989 | Greenquist | 422/56 |
| 4,855,240 | 8/1989 | Rosenstein et al. | 436/514 |
| 4,943,522 | 7/1990 | Eisinger | 435/7.25 |
| 4,959,307 | 9/1990 | Olson | 435/7.91 |
| 4,960,691 | 10/1990 | Gordon | 435/6 |
| 4,999,285 | 3/1991 | Stiso | 435/7.9 |
| 5,006,474 | 4/1991 | Horstman | 436/524 |
| 5,030,558 | 7/1991 | Litman | 435/7.91 |
| 5,037,736 | 8/1991 | Freitag | 435/7.9 |
| 5,039,607 | 8/1991 | Skold | 435/7.5 |
| 5,081,013 | 1/1992 | Rovelli | 435/7.92 |
| 5,236,826 | 8/1993 | Marshall | 435/7.92 |

FOREIGN PATENT DOCUMENTS

| | | |
|---|---|---|
| 0173375 | 3/1986 | European Pat. Off. . |
| 0212599 | 8/1986 | European Pat. Off. . |
| 0276152 | 7/1988 | European Pat. Off. . |
| 0306772 | 3/1989 | European Pat. Off. . |
| 0421294 | 4/1991 | European Pat. Off. . |
| 2204398 | 11/1988 | United Kingdom . |
| 8603839 | 7/1986 | WIPO . |
| 8702774 | 5/1987 | WIPO . |

OTHER PUBLICATIONS

Ngo in *Enzyme–Mediated Immunoassay*, pp. 3–19. (1985).
Tyhach et al, *Clinical Chemistry*, vol. 27, No. 9, pp. 1499–1504 (1981).
Greenquist et al, *Clinical Chemistry*, vol. 27, No. 9, pp. 1614–1617 (1981).
*Analytical Biochemistry*, vol. 85, 180–187 (1978).

*Primary Examiner*—Carol A. Spiegel
*Attorney, Agent, or Firm*—Robert M. Hallenbeck

[57] ABSTRACT

A chromatographic test strip comprising a solid support having at least a first portion and a second portion with said portions being in the same plane so as to permit capillary flow communication with each other. The sample is added to the first portion. The first portion also may comprise a tracer portion having a tracer movably supported therein. The tracer consists of a visible particulate marker. In the second portion, a binder is immobilized. The test strip is useful in a variety of immunoassays.

23 Claims, 1 Drawing Sheet

SOLID PHASE CHROMATOGRAPHIC IMMUNOASSAY

This application is a continuation of U.S. Ser. No. 07/818,000, filed 30 Dec. 1991 (now abandoned), which is a continuation of U.S. Ser. No. 07/031,023, filed 27 Mar. 1987 (now abandoned).

BACKGROUND OF THE INVENTION

This invention relates to an assay for an analyte, and more particularly to a solid phase assay.

FIELD OF THE INVENTION

Assays for various analytes have been accomplished by a so-called solid phase assay. In a solid phase assay, a binder specific for at least the ligand to be determined (analyte) is supported on a solid support, whereby, in the assay it is not necessary to employ an additional agent for separating the bound and free phases formed in the assay.

In general, such solid supports have been in the form of tubes, solid particles, and in some cases, the solid phase has been in the form of a "dip-stick".

In a dip-stick solid phase assay, a binder may be supported the dip-stick with the dip-stick, containing the binder, being dipped into an assay solution containing the analyte, and in general, such solution further contains a tracer. The presence and/or amount of tracer on the dip-stick is then employed as a measure of analyte (either a qualitative or quantitative measure of analyte).

The present invention is directed to providing an improved solid phase assay for determining analyte, and more particularly to a solid phase assay.

SUMMARY OF THE INVENTION

In accordance with one aspect of the present invention, there is provided a solid support having a first portion and a second portion with the first and second portions being in capillary flow communication with each other whereby material flows by capillarity. The first and second portions are positioned on the solid support in a manner such that the first portion may be contacted with material, including any analyte, with material in said first portion being transported by capillarity from the first portion of the support to the second portion thereof.

The second portion of the solid support includes a binder which is a binder for at least the analyte, with the binder also being a binder for a tracer used in the assay, when the assay format is a so-called competitive assay format.

The solid support also includes a tracer, which is comprised of a ligand portion and a detectable label portion conjugated to the ligand portion of the tracer. In the case where the assay format is a so-called competitive assay format, the ligand portion of the tracer is bound by the binder contained in the second portion of the solid support. In the case where the assay format is a so-called sandwich assay format, the ligand portion of the tracer is bound by the analyte.

The tracer is supported on the solid support on a tracer portion of the solid support in a manner such that when wetted, the tracer is capable of being transported by capillarity to the second portion of the solid support, and thereafter, depending on the presence and/or absence of analyte and/or the amount of analyte, as hereinafter explained in more detail, to a third portion of the solid support.

The tracer portion of the solid support may be a separate portion of the solid support or may be the first portion of the solid support (the portion to which sample is added).

The binder which is supported on the second portion of the solid phase is supported in a manner such that the binder remains immobile and is not transported by capillarity to the third portion of the solid support.

The third portion of the solid support may be a portion for detecting tracer which has been transported by capillarity from the second portion to the third portion. The third portion may or may not include a substance supported thereon for detecting tracer. Alternatively, the third portion may function only to receive materials not bound in the second portion.

In accordance with the present invention, the amount of tracer which is immobilized in the second portion of the solid support by being bound either directly to the binder in the second portion (in a competitive assay format), or by being indirectly bound to the binder (tracer is bound to analyte which is bound to the binder in a sandwich assay format) is dependent upon the presence and/or amount of analyte in the sample. In a so-called sandwich assay format, the amount of tracer which is passed from the second portion to the third portion of the solid support by capillarity is indirectly proportional to the amount of analyte in the sample, and in the so-called competitive assay format, the amount of tracer which passes from the second portion to the third portion of the solid support, by capillarity, is directly proportional to the amount of analyte in the sample.

In a preferred embodiment of the present invention, the solid support and the various components are produced and employed in a manner for determining analyte by a competitive assay format, with the tracer being supported on the first portion of the solid support.

In a particularly preferred embodiment, as hereinafter explained in more detail, the detectable label portion of the tracer is comprised of a sac or lipid vesicle (often referred to as a liposome), which includes a detectable label.

In employing a preferred embodiment wherein the assay is a competitive assay, the tracer is supported on the solid support on the first portion thereof, and the first portion of the solid support is wetted with the sample containing analyte to be determined. Upon wetting of the solid support with the sample, both sample and tracer flow by capillarity into the second portion of the solid support which contains a binder specific for both the analyte and tracer, with the binder being immobilized on the second portion of the solid support. Depending upon the presence and/or amount of analyte in the sample portion, tracer becomes bound to the binder on the second portion of the solid support. The tracer which is not bound by the binder on the second portion, then flows by capillarity into the third portion of the solid support for detection and/or determination therein. If the assay format is to be a simple "yes or no" format (only determining whether or not analyte is present in the sample), then the binder supported on the second portion of the solid support is supported in an amount such that in the absence of a detectable amount of analyte in the sample, there is no detectable presence of tracer in the third portion of the solid support. As should be apparent, as the amount of analyte in the sample increases, the amount of tracer which is not bound to the binder in the second portion of the solid support increases, thereby increasing the amount of tracer present in the third portion of the solid support. Accordingly, a quantitative assay may be run by determining tracer which remains in the second portion of the solid support and/or which flows by capillarity into the third portion of the solid support, and comparing such detected amount of tracer in the second and/or third portion with a "standard curve" to determine the amount of analyte in the sample. Thus, in an assay the determination of tracer and/or analyte may be either qualitative or quantitative.

In the sandwich assay format, tracer is preferably supported on a tracer portion of the solid support which is different from the first portion of the solid support. The ligand portion of the tracer is bound by the analyte, with the binder in the second portion of the solid support being specific for the analyte. The first portion of the solid support is contacted with the sample containing analyte, and the tracer portion of the solid support is wetted to cause both the tracer and analyte to flow by capillarity to the binder supported by the second portion of the support. The amount of tracer which becomes bound to analyte is directly proportional to the amount of analyte in the sample, and tracer bound to analyte, as well as any unbound tracer, flow by capillarity to the second portion of the solid support. In the second portion of the solid support, analyte becomes bound to immobilized binder specific for the analyte, with the unbound tracer (tracer not bound to analyte which is bound to the immobilized binder) flows by capillarity to the third portion of the solid support. The tracer on the third portion of the solid support may be detected as a measure of the presence and/or amount of analyte in the sample.

In a "yes or no" sandwich assay type format, the amount of tracer which is employed on the first portion of the solid support as well as the amount of binder on the second portion of the solid support are such that in the presence of a detectable amount of analyte, essentially no detectable tracer flows into the third portion of the solid support.

In a sandwich assay format, the amount of binder which is employed on the second portion of the solid support is an amount such that essentially all of the analyte which is suspected of being present in the sample is bound by the binder on the second portion.

The solid support which is employed in the assay is one which is capable of absorbing analyte from the sample, and which, when wetted, provides for flow of analyte and tracer by capillary attraction from the first portion, and through the second portion into the third portion of the solid support. In addition, the solid support is one which is capable of supporting tracer and the binder. As representative examples of suitable solid supports there may be mentioned: glass fiber, cellulose, nylon, crosslinked dextran, various chromatographic papers, nitrocellulose, etc. A particularly preferred material is nitrocellulose.

The solid support is preferably shaped in the form of a strip, with the first, second and third portions being arranged on the strip in the same plane in a manner such that material can flow by capillary attraction from the first zone and through the second zone to the third zone. Although the preferred shape is in the form of a strip, any other of a wide variety of shapes or forms may be employed as long as the shape and form permits separate portions for performing the various functions, as hereinabove described.

The tracer employed in the assay, as hereinabove indicated, is comprised of a ligand portion and a detectable label portion conjugated to the ligand portion. The detectable label of the detectable label portion may be any one of a wide variety of detectable labels; however, in accordance with a preferred embodiment, the detectable label is one which provides a color change in the second and/or third portion of the solid support, which is either a visible color change, or one which requires an instrument to detect the change in color. In accordance with a preferred embodiment, the label which is employed provides a change in color in the second and/or third portion of the solid support which is visible without the use of an instrument. For example, such a change in color may be provided by employing an enzyme as the detectable label, and by providing a substrate for the enzyme in the third portion of the solid support, which substrate, when contacted with the enzyme, provides a visible detectable change in color. Alternatively, the detectable label may be the substrate, and the third portion of the solid support may be provided with the enzyme, whereby there is a detectable change in color in the third portion by contacting of the enzyme with the substrate label. As representative examples of other detectable labels, which may or may not require an instrument for detecting a color change, there may be mentioned various chromogens, such as fluorescent materials, absorbing, dyes, and the like. As hereinafter indicated in a competitive assay, a preferred label portion is a vesicle, which includes a detectable marker, with the detectable marker being one which is visible.

The ligand portion of the tracer is dependent upon the assay format. If the assay is a competitive assay, then the ligand portion of the tracer is either the analyte or an appropriate analogue thereof. An appropriate analogue means that the analogue of the ligand is also specifically bound by the binder for the analyte. If the assay format is a sandwich type of assay, then the ligand portion of the tracer is a ligand which is specifically bound by the analyte or by an antibody which is specifically bound by the analyte.

The binder which is employed in the assay is one which at least binds the analyte. As hereinabove indicated, if the assay format is a competitive type of assay format, then the binder also binds the ligand portion of the tracer.

As generally known in the art, if the analyte is an antigen or a hapten, then the binder may be either a naturally occuring binder or an antibody which is specific for the analyte (either a polyclonal and/or monoclonal antibody). If the analyte is an antibody, the binder may be either an antigen specific for the antibody or an antibody which specifically binds the antibody analyte.

The binder may be supported on the solid support in a manner which immobilizes the binder; e.g., adsorption, covalent coupling, etc. The procedures for immobilizing binders on a solid support are generally known in the art.

The tracer, when supported on the first portion of the solid support, is supported in a manner such that when the first portion is wetted the tracer flows by capillary action. Thus, for example, the tracer may be absorbed on the first portion of the support.

In accordance with a particularly preferred embodiment of the present invention, in a competitive assay, the tracer is comprised of a ligand conjugated to a vesicle, which vesicle contains a detectable marker, with the tracer being supported on the solid support. Applicant has found that it is possible to support such a tracer on a solid support of the type hereinabove described, and that such tracer will flow by capillarity when the solid support is wetted with a sample containing or suspected of containing an analyte.

The lipid vesicles (liposomes) which are employed may be prepared from a wide variety of lipids, including phospholipids, glycol lipids, and as representative examples there may be mentioned lecithin, spingomyelin, dipalmitoyl lecithin, distearoylphosphatidylcholine, etc. The amphiphilic lipids employed for producing liposomes generally have a hydrophilic group, such as a phosphato, carboxylic, sulfato, or amino group, and a hydrophobic group, such as saturated and unsaturated aliphatic hydrocarbons, and aliphatic hydrocarbon groups substituted by one or more aromatic or cycloaliphatic groups. The wall forming compounds for producing the liposomes may further include a steroid component such as cholesterol, cholestanol, and the like. The compounds for producing liposomes are generally known in the art, and no further details in this respect are deemed necessary for a complete understanding of the present invention.

The liposomes may be produced by procedures generally available in the art. For example, liposomes may be produced by a reverse phase evaporation technique wherein the compound or compounds used in producing liposomes are initially dissolved in an organic phase, followed by addition of an aqueous phase and forming of a homogeneous emulsion. After forming the emulsion, the organic solvent is evaporated to form a gel like material, and such gel may be converted to a liposome by agitation or dispersion in an aqueous media.

Procedures for producing liposomes are described, for example, in U.S. Pat. No. 4,241,046; U.S. Pat. No. 4,342,828 and PCT International Publication No. WO 80-01515.

If a material is to be encapsulated in the liposome, such material may be encapsulated in the liposome by including the material in the aqueous solution in which the liposome is formed. Alternatively, the material may be encapsulated into a previously formed empty liposome (without material to be encapsulated) by the procedure described in U.S. Pat. No. 4,539,376.

The liposomes may also be produced by the procedures disclosed in U.S. Pat. No. 4,522,803.

The material which is entrapped or encapsulated within the liposome (the material is within the aqueous compartment or within the membrane bilayer of the liposome) is a detectable marker, such as dyes, radiolabels, fluorescent materials, chemiluminescent materials, electron spin resonance materials, and the like; substrates for detectable markers; and the like. Alternatively, the liposome may be derivatized with a detectable marker, rather than entrapping a marker in the liposome.

The liposome is derivatized with a ligand for producing a tracer. The liposome may be derivatized with a ligand by procedures known in the art, such as covalent coupling, derivatization or activation, etc. In derivatizing the liposomes with a ligand, a compound or compounds used in forming the liposome may be derivatized with the ligand, prior to forming the liposome, or alternatively, the liposome may be derivatized with the ligand, subsequent to forming of the liposome. Procedures for derivatizing liposomes with ligands, and suitable coupling agents, and the like for preparing derivatized liposomes are known in the art, and no further details in this respect are deemed necessary for a complete understanding of the present invention.

In employing a preferred tracer in which the detectable marker portion thereof is comprised of liposome including a detectable marker for use in a competitive assay, the assay may be accomplished as hereinabove described with general reference to a variety of tracers, except that the tracer includes a liposome as the detectable marker portion of the tracer.

In a particularly preferred embodiment, the tracer used in the assay is a ligand conjugated to a particulate label which is visible. The term "visible" as used herein means that the label can be seen without the use of instrumentation; i.e., with the naked eye. The particulate label is may be a metal or alloy (e.g. colloidal gold) or a sac in particular a liposome containing a visible dye. The marker preferably included in the sac is a dye or some other material which is visible, without lysing of the sacs.

The tracer comprised of ligand and particulate label may also be produced by labeling the ligand with an aqueous dispersion of a hydrophobic dye or pigment, or of polymer nuclei coated with such a dye or pigment. Such labels are described in more detail in U.S. Pat. No. 4,373,932, which issued on Feb. 15, 1983. The tracers produced in accordance with such patent may also be employed as tracers in the present invention.

As indicated in the aforesaid patent, the colored organic compounds which are used as labels are in the form of a hydrophobic sol, which hydrophobic organic dyes or pigments are insoluble in water or soluble only to a very limited extent.

The visible particulate label may be visible polymer particles, such as colored polystyrene particles, preferably of spherical shape.

As representative examples of other particulate labels which may be employed in producing a tracer for use in the assay of the present invention, in which the tracer would be visible, there may be mentioned; ferritin, phycoerythrins or other phycobili-proteins; precipitated or insoluble metals or alloys; fungal, algal, or bacterial pigments or derivatives such as bacterial chlorophylls; plant materials or derivative metal sols and the like. In such an embodiment, at least the portion of the product which includes the binder is formed of a material having a surface area capable of supporting the binder thereon in an amount such that tracer bound in such portion is visible. In general, the surface area is capable of supporting the binder in a concentration of at least 1 ug/cm$^2$, and most generally in a concentration of at least 10 ug/cm$^2$. A particularly preferred material is nitro-cellulose. Such materials and tracers are described in U.S. Pat. No. 4,703,017, which is hereby incorporated by reference.

BRIEF DESCRIPTION OF THE DRAWING

Referring to FIG. 1, there is shown a strip 10 including a first portion A on which a tracer is supported; a second portion B on which a binder is supported and a third portion D in which tracer may be determined. As particularly shown, a portion C is between portions B and D to provide spacing between portions B and D, whereby the portion for determining tracer is separated by a distance from the portion containing binder.

Figure 1:
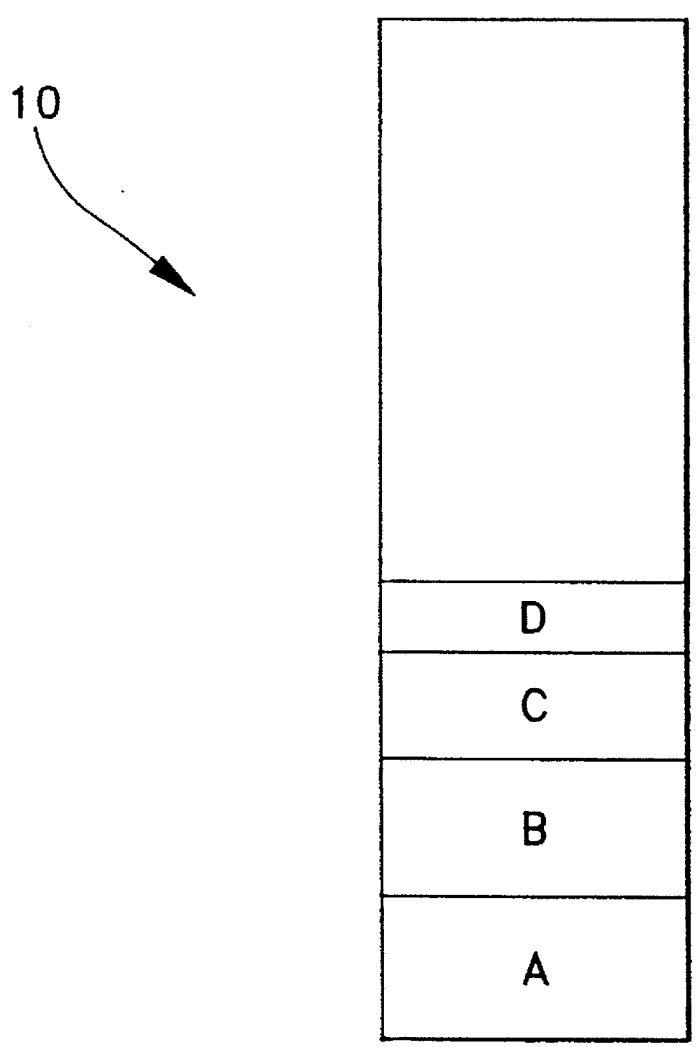
FIG. 1 is a schematic representation of a chromatographic test strip wherein "A" represents the first portion of the test strip, "B" represents the second portion of the test strip and "C" and "D" represent a third portion of the test strip.

In a competitive assay format, employing an enzyme as a detectable label, portion A would contain ligand labeled with enzyme, with the ligand portion being the analyte or appropriate analogue thereof; portion B would contain a binder specific for the analyte and the ligand portion of the tracer; and portion D would contain a substrate for the enzyme which interacts with the enzyme to provide a change in color.

In use, portion A of the strip 10 would be contacted with a sample containing analyte, whereby portion A would be wet with the sample. The tracer in portion A, as well as, sample would be transported by capillarity to portion B, where tracer and analyte compete for binding sites on the binder. Unbound tracer and unbound analyte move by capillarity through portion C to portion D where any tracer interacts with the substrate in portion D to provide a change in color. As hereinabove indicated, the assay may be a "yes-no" assay or a quantitative assay and detection of tracer in portion D is dependent upon the assay employed.

In the case where the tracer has a detectable label which does not require an additional substance for determination thereof, the portion D would not require an additional substance, i.e., portion D would also be blank. Thus, for example if the tracer included a liposome having a dye as a detectable label, then tracer may be determined without supporting an additional substance on portion D. Alternatively, if for example, it was required to release detectable lable from the liposome, portion D could contain a suitable lysing agent, such as an enzyme or detergent which lyses liposomes to release label from the liposome in portion D for detection of tracer.

In addition, it is also possible to determine tracer in portion C, with or without determining tracer in portion D. For example, a substrate could be added to portion C in the case where the label is an enzyme.

The product may be used as a dip stick. Alternatively, a sample may be applied to portion A. Accordingly, the product may be used in either a horizontal or vertical orientation.

The invention is applicable to detecting and/or measuring a wide variety of analytes, such as: drugs, including therapeutic drugs and drugs of abuse; hormones, vitamins, proteins, including antibodies of all classes, peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hCG; insulin; theophylline; leutinizing hormone; organisms causing or associated with various disease states, such as *Streptococcus pyogenes* (group A), Herpes Simplex I and II, cytomegalovirus, chlamydia, rubella antibody, etc.

The invention will be further described with reference to the following example:

EXAMPLE

Dipsticks were constructed by first coating 0.5×8 cm strips of polystyrene with Scotch® #969 adhesive transfer tape (3M, St. Paul Minn. 55144). Zone B, consisting of a 0.5×0.5 cm square of 5 um-pore nitrocellulose (S&S, Keene, N.H.) was spotted with 3 ul of affinity purified rabbit anti-Group A *Streptococcus* antigen and then blocked with 3% bovine serum albumin. After drying, it was applied to the taped side of the dipstick, approximately 1 cm from the bottom of the stick. A strip of filter paper 0.5×6.5 cm. (Whatman 3 mm) was applied just above and touching the nitrocellulose, at the positions indicated by zones C and D. Zone A, consisting of dry SEPHADEX G50 fine grade bead-formed gel of cross-linked dextran (Pharmacia) was then applied.

DETAILED DESCRIPTION

Detector liposomes packed with sulfo-rhodamine dye were prepared by the method outlined in O'Connell et al. (Clin. Chem. 31:1424 [1985]). They were covalently coupled to affinity purified rabbit anti-Group A *Streptococcus* antigen.

The detector liposomes were spotted (2 ul) onto Zone A, 0.5 cm from the bottom and air dried. The liposomes are in a 0.05M Tris buffer, pH 6.8, containing 2% glycerol, 0.05% dimethyl sulfoxide, 20 mM EDTA.

Group A *Streptococcus* organisms were harvested from culture plates, washed with saline (0.9% NaCl), and adjusted to $1\times10^9$ organisms/ml. An aliquot (0.1 ml) containing $1\times10^8$ organisms was subjected to the micro nitrous acid extraction method for exposing the Group A carbohydrate antigen. This method consists of mixing 0.3 ml of 0.1M HCl with 40 ul of 4M $NaNO_2$, adding this to the *Streptococcus* organisms and, after 3 minutes, neutralizing with 40 ul of 1M Tris base. To faciliate the extraction and the dipstick assay, the HCl and the subsequent diluting fluid contain 0.1% Tween-20 non-ionic detergent.

Using the extracted antigen, a dilution series was prepared ranging from $8\times10^6$ organisms/ml to $1.25\times10^5$ organisms/ml. Aliquots of these dilutions (0.5 ml) were placed in 12×75 mm test tubes and a dipstick placed into the fluid in each test tube. As the fluid containing extracted antigen wicks up the stick, it carries the liposome detector past the spot of capture antibody. In the presence of antigen, which binds to the capture antibody spot, some of the liposomes also bind, resulting in the appearance of a red spot in zone B. The remainder of the liposomes and antigen solution pass into zone D.

The assay can be "read" by observing the lowest concentration of organisms resulting in a red spot in zone B. The results of this example are given in the following table and indicate the an end point of $5\times10^5$ organisms/ml, close to the sensitivity required for a direct throat swab diagnostic for Group A *Streptococcus* pharyngitis.

| Group A Strep Antigen (organisms/ml) × $10^{-5}$ | | | | | | | |
| --- | --- | --- | --- | --- | --- | --- | --- |
| 80 | 40 | 20 | 10 | 5 | 2.5 | 1.25 | 0 |
| + | + | + | + | + | − | − | − |

(+) = positive indication of antigen (red spot)
(−) = negative indication of antigen (red spot)

The present invention is advantageous in that there is provided a product and process which may be easily employed for accomplishing an assay. The product and process do not require the addition of tracer in that tracer is included in the product. In addition, the product and process are capable of providing for a rapid assay.

These and other advantages should be apparent to those skilled in the art from the teachings herein.

Numerous modifications and variations of the present invention are possible in light of the above teachings; therefore, the invention may be practiced otherwise than as particularly described.

What is claimed is:

1. A test strip for determining the presence of an analyte in a liquid sample comprising a solid support, said solid support comprising at least a first portion and a second portion, said portions being in the same plane so as to permit capillary flow communication with each other;

said first portion being the site for application of the liquid sample and further comprising a tracer site, said tracer site consisting of a tracer movably supported therein wherein said tracer comprises a ligand, which specifically binds to the analyte, conjugated to a visible particulate marker; and said second portion being the site for visually determining the presence of the visible particulate marker, said second portion consisting of a binder immobilized therein which specifically binds to the analyte.

2. The test strip of claim 1 wherein the solid support comprises nitrocellulose.

3. The test strip of claim 1 wherein the visible particulate marker is selected from the group consisting of colloidal metals, colored liposomes, colored polymeric beads and polymerized dye molecules.

4. The test strip of claim 3 wherein the visible particulate marker is a colored liposome.

5. The test strip of claim 3 wherein the visible particulate marker is a colored polymeric bead.

6. The test strip of claim 1 wherein the analyte is an antigen and the ligand and the binder are antibodies thereto.

7. The test strip of claim 1 wherein the ligand and the binder are antigens or analogs thereof and the analyte is an antibody thereto.

8. The test strip of claim 1 wherein the first portion and the tracer portion are spatially separate from each other with the first portion being upstream of the tracer portion.

9. A no-wash, one-step method for determining the presence of an analyte in a liquid sample consisting of the steps of:
   a) adding a liquid sample to the first portion of the test strip of claim 1;
   b) allowing sufficient time for the liquid sample to flow to the second portion of the test strip; and
   c) determining the presence of the analyte in the liquid sample by visual inspection of the second portion for the visible particulate marker wherein the presence of the analyte is indicated by the presence of the visible particulate marker.

10. The method of claim 9 wherein the liquid sample is added to the test strip by immersing the first portion into the liquid sample.

11. A test strip for determining the amount of an analyte in a liquid sample comprising a solid support, said solid support comprising at least a first portion and a second portion, said portions being in the same plane so as to permit capillary flow communication with each other;
   said first portion being the site for application of the liquid sample and further comprising a tracer site, said tracer site consisting of a tracer movably supported therein wherein said tracer comprises a ligand, which is the analyte or an analog thereof, conjugated to a visible particulate marker; and
   said second portion being the site for visually determining the amount of the visible particulate marker, said second portion consisting of a binder immobilized therein which specifically binds to the ligand.

12. The test strip of claim 11 which consists of a third portion in the same plane as the first and the second portions, all of said portions being in capillary flow communication with each other, and said third portion being an additional site for visually determining the amount of visible particulate marker bound therein.

13. The test strip of claim 11 wherein the visible particulate marker is selected from the group consisting of colloidal metals, colored liposomes, colored polymeric beads and polymerized dye molecules.

14. The test strip of claim 13 wherein the visible particulate marker is a colored liposome.

15. The test strip of claim 13 wherein the visible particulate marker is a colored polymeric bead.

16. The test strip of claim 11 wherein the analyte is an antigen.

17. The test strip of claim 11 wherein the analyte is an antibody.

18. The test strip of claim 11 wherein the first portion and the tracer portion are spatially separate from each other with the first portion being upstream of the tracer portion.

19. A no-wash, one-step method for determining the presence of an analyte in a liquid sample consisting of the steps of:
   a) adding a liquid sample to the first portion of the test strip of claim 11;
   b) allowing sufficient time for the liquid sample to flow to the second portion of the test strip; and
   c) determining the presence of the analyte in the liquid sample by visual inspection of the second portion for the visible particulate marker wherein the presence of the analyte is indicated by the absence of the visible particulate marker.

20. A no-wash, one-step method for determining the amount of an analyte in a liquid sample consisting of the steps of:
   a) adding a liquid sample to the first portion of the test strip of claim 12;
   b) allowing sufficient time for the liquid sample to flow to the second portion and the third portions of the test strip; and
   c) determining the amount of the analyte present in the liquid sample by visual inspection of the second portion and the third portion for the amount of the visible particulate marker bound in each portion wherein the presence of the analyte is indicated by the absence of the visible particulate marker.

21. The method of claim 19 wherein the liquid sample is added to the test strip by immersing the first portion into the liquid sample.

22. The method of claim 20 wherein the liquid sample is added to the test strip by immersing the first portion into the liquid sample.

23. The test strip of claim 11 wherein the solid support comprises nitrocellulose.

* * * * *